United States Patent
Morita et al.

(10) Patent No.: US 7,525,554 B2
(45) Date of Patent: Apr. 28, 2009

(54) CONTENT BASED HANGING PROTOCOLS FACILITATED BY RULES BASED SYSTEM

(75) Inventors: Mark M. Morita, Arlington Heights, IL (US); Prakash Mahesh, Schaumburg, IL (US); Thomas A. Gentles, Algonquin, IL (US)

(73) Assignee: General Electric Company, Schenectady, NY (US)

( * ) Notice: Subject to any disclaimer, the term of this patent is extended or adjusted under 35 U.S.C. 154(b) by 560 days.

(21) Appl. No.: 11/028,768

(22) Filed: Jan. 3, 2005

(65) Prior Publication Data

US 2006/0146071 A1    Jul. 6, 2006

(51) Int. Cl.
*G09G 5/00* (2006.01)
(52) U.S. Cl. .................. 345/619; 382/128; 715/745; 715/765
(58) Field of Classification Search .............. 345/419, 345/619; 707/1, 10; 715/854, 745, 764; 382/128

See application file for complete search history.

(56) References Cited

U.S. PATENT DOCUMENTS

| | | | |
|---|---|---|---|
| 5,774,661 A | | 6/1998 | Chatterjee et al. |
| 5,781,247 A | * | 7/1998 | Wehmeyer et al. ......... 348/569 |
| 5,821,936 A | * | 10/1998 | Shaffer et al. ............... 715/810 |
| 6,243,095 B1 | * | 6/2001 | Shile et al. .................. 715/854 |
| 6,498,613 B1 | * | 12/2002 | Wajima ....................... 715/775 |
| 6,546,364 B1 | | 4/2003 | Smirnov et al. |
| 6,574,629 B1 | * | 6/2003 | Cooke et al. ................... 707/10 |
| 6,707,476 B1 | * | 3/2004 | Hochstedler ................ 715/789 |
| 2002/0052851 A1 | * | 5/2002 | Berman ........................ 705/64 |
| 2002/0055917 A1 | * | 5/2002 | Muraca .......................... 707/1 |
| 2002/0101436 A1 | * | 8/2002 | Shastri et al. ............... 345/619 |
| 2004/0202387 A1 | * | 10/2004 | Yngvesson .................. 382/305 |
| 2004/0252871 A1 | * | 12/2004 | Tecotzky et al. ............ 382/128 |
| 2005/0021472 A1 | * | 1/2005 | Gettman et al. ............... 705/52 |
| 2005/0025349 A1 | * | 2/2005 | Crewe ........................ 382/128 |
| 2005/0110788 A1 | * | 5/2005 | Turner et al. ................ 345/419 |

* cited by examiner

*Primary Examiner*—Kee M Tung
*Assistant Examiner*—Michelle K Lay
(74) *Attorney, Agent, or Firm*—McAndrews, Held & Malloy, Ltd.; Peter J. Vogel; Michael A. Dellapenna (57) ABSTRACT

The present invention provides a computer-readable storage medium including a set of instructions for a computer. The instructions include an access routine, a tracking routine, and a modifying routine. The access routine is configured to communicate a default hanging protocol between a network server and a display workstation. The default hanging protocol includes at least one default display rule for displaying a plurality of images at the display workstation. The default display rule is capable of directing the display workstation to present each of the images at a location on a display device of the display workstation and/or in a sequence in which each of the images is presented at the display workstation. The tracking routine is configured to monitor a selection of an additional display rule. The modifying routine is configured to dynamically modify the default hanging protocol based on the selection.

26 Claims, 5 Drawing Sheets

CONTENT BASED HANGING PROTOCOLS FACILITATED BY RULES BASED SYSTEM

BACKGROUND OF THE INVENTION

The present invention generally relates to an improvement in customization of automatic image presentation. Specifically, the present invention relates to the dynamic modification of hanging protocols based on a user's selection of additional display rules.

Picture archiving and communication systems ("PACS") connect to medical diagnostic imaging devices and employ an acquisition gateway (between the acquisition device and the PACS), storage and archiving units, display workstations, databases, and sophisticated data processors. These components are integrated together by a communication network and data management system. A PACS has, in general, the overall goals of streamlining health-care operations, facilitating distributed remote examination and diagnosis, and improving patient care.

A typical application of a PACS system is to provide one or more medical images for examination by a medical professional. For example, a PACS system can provide a series of x-ray images to a display workstation where the images are displayed for a radiologist to perform a diagnostic examination. Based on the presentation of these images, the radiologist can provide a diagnosis. For example, the radiologist can diagnose a tumor or lesion in x-ray images of a patient's lungs.

However, before a user is able to view images on a display workstation, the images may undergo preprocessing and processing. In other words, preprocessing and processing functions are applied to images before a user views the images. For example, when raw image data (image data that is received from an imaging modality and has not undergone any preprocessing or processing) is initially received by a PACS system, one or more preprocessing functions are applied to the raw image data. Typically, the preprocessing functions applied to raw image data are modality-specific enhancements. Modality-specific enhancements can include, for example, contrast or frequency compensation functions specific to a particular x-ray imaging device. For example, contrast preprocessing functions may be characterized by the following parameters: GT (contrast type), GA (rotation amount of GT curve), GC (rotation center for GT), and GS (density shift, the amount of shifting applied to GT). The frequency preprocessing functions may be characterized by the following parameters: RN (frequency rank), RE (frequency enhancement), and RT (frequency type). Each preprocessing function may represent a linear or non-linear function, function modification, or function parameter. The preprocessing functions may be applied to raw image data any time prior to the image processing and display.

The preprocessing functions may be selected based, for example, on an anatomical region to which the raw image data corresponds. In other words, the preprocessing functions selected may vary depending on whether the raw image data represents, as examples, the head, neck, chest, abdomen, breast, lungs, pelvis, or shoulders. The preprocessing functions may vary for each anatomical region due to the differences in tissue, bone, and blood vessel density and prevalence.

Once the image data has been preprocessed, a user can access the image data from a display workstation. In general, one or more images representing the image data are displayed on the display workstation. The images typically are displayed in a particular spatial layout and/or temporal sequence. In other words, the images may be displayed in certain positions on a display device relative to each other (a spatial layout, for example). The images may also be displayed in a certain ordered sequence by displaying image A first, followed by image B, followed by image C, and so on (a temporal sequence, for example). The spatial and/or temporal presentation of images is directed by a set of display rules. A display rule may include a set of instructions stored on a computer-readable media that direct the presentation of images on a display workstation. A set of display rules is known as a hanging protocol. In general, a hanging protocol is a series of display rules that dictate the spatial and/or temporal layout and presentation of a plurality of images.

However, the user may desire to employ additional display rules to alter or modify a presentation of images at a display device. For example, the user may wish to present additional images adjacent to currently displayed images. In another example, the user may wish to present additional images after the current images are reviewed.

With increasing volumes of examinations and images, a reduction of radiologists and mounting pressures on improved productivity, radiologists are in dire need of reducing the amount of their time spent customizing hanging protocols to meet their individual preferences. In addition, radiologists expend a considerable amount of time adjusting a presentation of images at a display workstation after a computer-aided diagnosis ("CAD") has revealed one or more objects of interest in the images. For example, after a CAD reveals a possible lesion in a patient anatomy, the radiologist may then wish to display previously acquired images of the same patient anatomy to see if any change has occurred in the anatomy. As the default hanging protocol does not automatically display the previously acquired images, the radiologist must search for the images and wait for the images to load in a preferred location and sequence before reviewing the images.

Typically, radiologists must repeatedly select the same or similar display rules to be applied to a set of images (after a default hanging protocol has been employed to present the images in a default manner). In addition, radiologists repeatedly select a same or similar sequence of display rules to be applied to a set of images (again, after a default hanging protocol has been employed to present the images in a default manner). A considerable amount of time is spent repeatedly selecting the same display rules or the same sequence of display rules. Therefore, a need exists for reducing and alleviating rote, repetitive tasks (such as repeatedly selecting the same display rules or sequence of display rules). Such a need can be met by dynamically modifying default hanging protocols so as to incorporate display rules repeatedly selected by a radiologist, for example. Doing so would allow radiologists to more quickly obtain images that are automatically displayed according to their individual preferences. The user may then focus more of their time on the primary task of diagnosis.

BRIEF SUMMARY OF THE INVENTION

The present invention provides a computer-readable storage medium including a set of instructions for a computer. The instructions include an access routine, a tracking routine, and a modifying routine. The access routine is configured to communicate a default hanging protocol between a network server and a display workstation. The default hanging protocol includes at least one default display rule for displaying a plurality of images at the display workstation. The default display rule is capable of directing the display workstation to present each of the images at a location on a display device of the display workstation and/or in a sequence in which each of the images is presented at the display workstation. The tracking routine is configured to monitor a selection of an additional display rule. The modifying routine is configured to dynamically modify the default hanging protocol based on the selection.

The present invention also provides method for dynamically altering a default hanging protocol. The method includes providing access to the default hanging protocol, providing a tracking system capable of monitoring a selection of an additional display rule, and providing a hanging protocol editor capable of dynamically creating a modified default hanging protocol. The display rule is employed to direct a display workstation to present each of a plurality of images in a location on a display device and/or in a sequence in which each of the images is presented on the display device. The modified default hanging protocol includes the default hanging protocol and a modification to the default hanging protocol. The modification is based on at least the selection of at least one additional display rule.

The present invention also provides a system for dynamically altering a hanging protocol in a picture archiving and communication system. The system includes a default hanging protocol including a subset of a plurality of display rules, a tracking system configured to monitor a user's selection of one or more display rules to alter a presentation of images, and a hanging protocol editor configured to modify the default hanging protocol based on at least the user's selection. The display rules are employed in determining a presentation of a plurality of images as displayed on a display device.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 1:
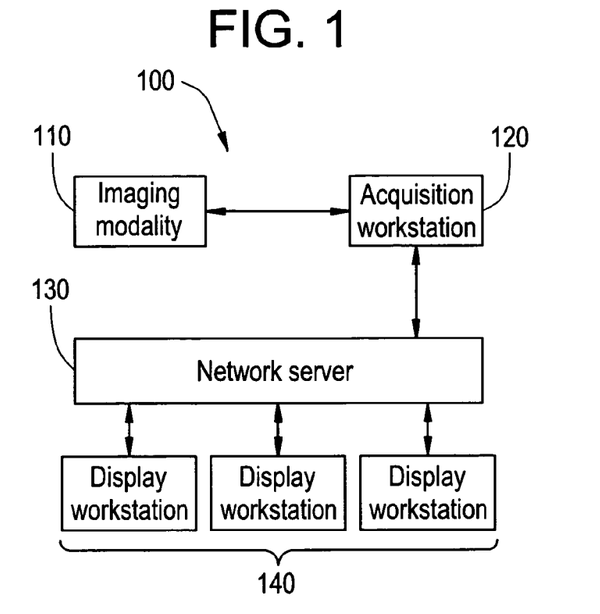
FIG. 1 illustrates an exemplary PACS system in accordance with an embodiment of the present invention.

FIG. 1 illustrates an exemplary PACS system 100 in accordance with an embodiment of the present invention. PACS system 100 includes an imaging modality 110, an acquisition workstation 120, a network server 130, and one or more display workstations 140. System 100 can include any number of imaging modalities 110, acquisition workstations 120, network servers 130 and display workstations 140 and is not in any way limited to the embodiment of system 100 as illustrated in FIG. 1.

In operation, imaging modality 110 obtains one or more images of a patient anatomy. Imaging modality 110 can include any device capable of capturing an image of a patient anatomy such as a medical diagnostic imaging device. For example, imaging modality 110 can include an X-ray imager, ultrasound scanner, magnetic resonance imager, or the like. Image data representative of the image(s) is communicated between imaging modality 110 and acquisition workstation 120. The image data can be communicated electronically over a wired or wireless connection.

Acquisition workstation 120 may apply one or more pre-processing functions to the image data in order to prepare the image for viewing on a display workstation 140. For example, acquisition workstation 120 may convert raw image data into a DICOM standard format or attach a DICOM header. The preprocessing functions are characterized in that they are modality specific enhancements (for example, contrast or frequency compensation functions specific to a particular X-ray imaging device, for example) applied at the beginning of the imaging and display chain.

The image data may then be communicated between acquisition workstation 120 and network server 130. The image data can be communicated electronically over a wired or wireless connection.

Network server 130 can include a computer-readable storage medium suitable for storing the image data for later retrieval and viewing at a display workstation 140. Network server 130 can also include one or more software applications for additional processing and/or preprocessing of the image data by one or more display workstations 140, as described below.

One or more display workstations 140 are capable of or configured to communicate with server 130. Display workstations 140 can include a general purpose processing circuit, a network server 130 interface, a software memory, and an image display monitor. The network server 130 interface may be implemented as a network card connecting to a TCP/IP based network, but may also be implemented as a parallel port interface, for example.

Display workstations 140 may retrieve or receive image data from server 130 for display to one or more users. For example, a display workstation 140 may retrieve or receive image data representative of a computed radiography ("CR") image of a patient's chest. A radiologist may then examine the image as displayed on a display device for any objects of interest such as, for example, tumors, lesions, etc.

Display workstations 140 are also capable of or configured to retrieve and/or receive one or more hanging protocols from server 130. For example, a default hanging protocol may be communicated to display workstation 140 from server 130. A hanging protocol may be communicated between server 130 and a display workstation 140 over a wired or wireless connection, for example.

In general, display workstations 140 may present images representative of image data retrieved and/or received from server 130. Display workstations 140 may present the images according to a hanging protocol. As described above, a hanging protocol is a set of display rules for presenting, formatting and otherwise organizing images on a display device of a display workstation 140. A display rule is a convention for presenting one or more images in a particular temporal and/or spatial layout or sequence. For example, a hanging protocol may include a set of computer-readable instructions (or display rules, for example) that direct a computer to display a plurality of images in certain locations on a display device and/or display the plurality of images in a certain sequence or order. In another example, a hanging protocol may include a set of computer-readable instructions that direct a computer to place a plurality of images in multiple screens and/or viewports on a display device. In general, a hanging protocol may be employed to present a plurality of images for a diagnostic examination of a patient anatomy featured in the images.

A hanging protocol may direct, for example, a display workstation 140 to display an anterior-posterior ("AP") image adjacent to a lateral image of the same anatomy. In another example, a hanging protocol may direct display workstation 140 to display the AP image before displaying the lateral image. In general, a hanging protocol dictates the spatial and/or temporal presentation of a plurality of images at display workstation 140.

A hanging protocol differs from a default display protocol ("DDP"). In general, a DDP is a default workflow that applies a series of image processing functions to image data. The image processing functions are applied to the image data in order to present an image (based on the image data) to a user. The image processing functions alter the appearance of image data. For example, an image processing function may alter the contrast level of an image.

DDPs typically include processing steps or functions that are applied before any diagnostic examination of the images. For example, processing functions may be applied to image data in order to enhance features within an image (based on the image data). Such processing functions can include any software-based application that may alter a visual appearance or representation of image data. For example, a processing function can include any one or more of flipping an image, zooming in an image, panning across an image, altering a window and/or level setting in a representation of the image data, and altering a contrast and/or brightness setting in a representation of the image data.

DDPs are usually based on a type of imaging modality used to obtain the image data. For example, image data obtained with a C-arm imaging device in general or a particular C-arm imaging device may have a same or similar DDP applied to the image data. In general, a DDP attempts to present image data in a manner most useful to many users.

Conversely, applying a hanging protocol to image data does not alter the appearance of an image (based on the image data), but instead dictates how the image(s) is(are) presented, as described above.

Server 130 may store a plurality of hanging protocols. The hanging protocols that are stored at server 130 and have not yet been modified or customized are default hanging protocols. A default hanging protocol may be selected from a plurality of default hanging protocols based on any number of relevant factors such as, for example, a manual selection of the default hanging protocol, a user identity, and/or pre-processing of the image data.

Specifically, a default hanging protocol may be selected based on a manual selection simply by communicating the default hanging protocol once a user has selected that particular protocol. The user may make the selection, for example, at a display workstation 140.

In another example, a default hanging protocol may be selected based on a user identity. For example, a user may have a preferred default hanging protocol. The hanging protocol may have been customized to meet the user's preferences for a particular temporal and/or spatial layout of images. Once a user gains access to a display workstation 140 (for example, by entering a correct login and password combination or some other type of user identification procedure), the preferred default hanging protocol may be communicated to the display workstation 140, for example.

In another example, a default hanging protocol may be selected based on pre-processing of image data. Pre-processing of image data may include any image processing known to those of ordinary skill in the art that prepares an image for review by a user. Pre-processing may also include, for example, a computer-aided diagnosis ("CAD") of image data. CAD of image data may include a computer (or similar operating unit) automatically analyzing image data for objects of interest. For example, a CAD may include a software application that analyzes image data for nodules in images of lungs, lesions, tumors, etc. However, a CAD application can include any automatic analysis of image data known to those of ordinary skill in the art.

CAD of image data may reveal one or more CAD findings. A CAD finding may include any object of interest in an image found by a CAD application. For example, a CAD finding may include a lung nodule, lesion, or tumor that appears in one or more images of a patient's lungs.

Image data may undergo CAD before a default hanging protocol is selected. A default hanging protocol may then be selected for the images based on CAD findings. The default hanging protocol selected for the images (based on the image data) may then be communicated between server 130 and workstation 140. The default hanging protocol may then be applied to the images at the workstation 140, as described above, in order to present the images in a spatial and/or temporal layout according to a hanging protocol that corresponds to the CAD findings. By basing which default hanging protocol is selected on CAD findings, the hanging protocol applied to a set of images is image content-based.

For example, a C-arm x-ray imaging device may obtain a plurality of x-ray images of a patient's lungs. The images may include a PA image and a lateral image of the patient's lungs. Image data corresponding to the images may then undergo CAD. The CAD may discover one or more objects of interest in the images that may correspond to lung tumors. In order to confirm that the CAD findings are lung tumors, a radiologist at a workstation 140 must examine the images according to a default hanging protocol that corresponds to CAD findings of lung tumors.

A default hanging protocol that corresponds to CAD findings of lung tumors may provide for the presentation of the PA and lateral lung images adjacent to each other followed by the presentation of the CT lung images, followed by the MR lung images, for example. In general, a default hanging protocol that corresponds to CAD findings is designed to present images in a spatial and/or temporal layout that is useful to a radiologist. For example, a radiologist may be greatly assisted in his or her review of the CAD findings by viewing the PA and lateral lung images adjacent to each other, followed by previously acquired multi-slice computed tomography ("CT") and magnetic resonance ("MR") images of the lungs.

Therefore, based on CAD findings, a default hanging protocol may be selected from a plurality of default hanging protocols and applied at a workstation 140 in order to present images to a user.

Figure 2:
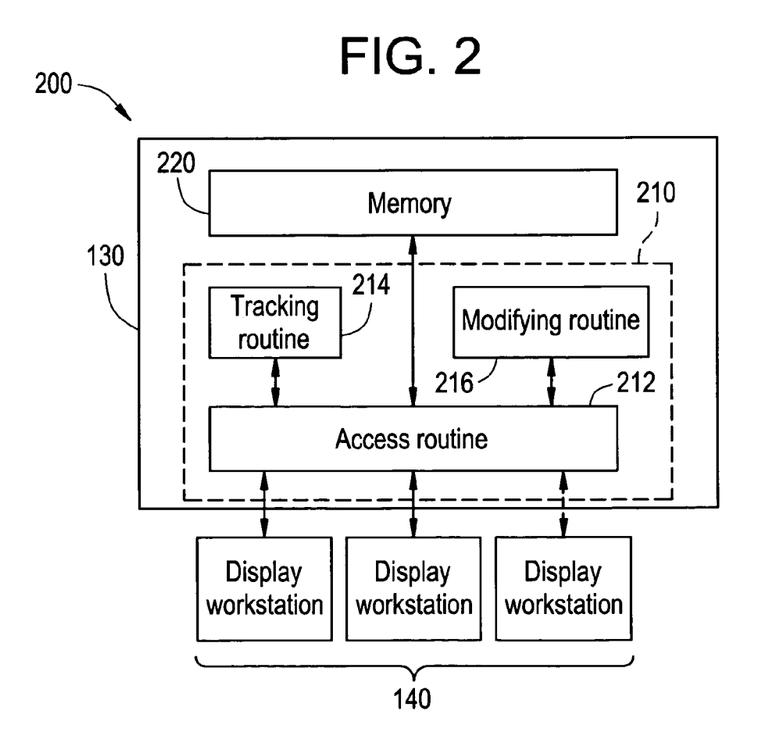
FIG. 2 illustrates a network server in accordance with an embodiment of the present invention.

FIG. 2 illustrates network server 130 in accordance with an embodiment of the present invention. Network server 130 includes a computer-readable storage medium 210 and a memory 220. Storage medium 210 includes a set of instructions for a computer. The instructions may be embodied in a software application that is stored on storage medium 210, for example. The instructions include an access routine 212, a tracking routine or system 214, and a modifying routine or hanging protocol editor 216. Memory 220 includes any computer-readable storage medium. Memory 220 may be used to store any one or more of image data, default hanging protocols or any other type of information that may be stored on computer-readable media. While server 130 is illustrated with only one memory 220, in accordance with the present invention, server 130 may include any number of memories 220. For example, server 130 may include a plurality of memories 220, each dedicated to the storage of a different type of image data.

In operation, a default hanging protocol is communicated from server 130 to a workstation 140. In general, access routine 212 is implemented on server 130 to direct server 130 to communicate a default hanging protocol from server 130 to workstation 140. Communication of the default hanging protocol between server 130 and display workstation 140 may occur over a network. For example, a user may log onto a display workstation 140 and connect the display workstation 140 to server 130 (and therefore access routine 212) for communication of a default hanging protocol between server 130 and workstation 140.

Once display workstation 140 is connected to server 130, the user may manually select a default hanging protocol from a list graphically displayed on display workstation 140. Once the user has made his or her selection, access routine 212 may retrieve or receive the selected default hanging protocol from memory 220.

In another embodiment of the present invention, a default hanging protocol is automatically selected based on an identity of a user at a workstation 140, as described above.

In another embodiment of the present invention, a default hanging protocol is automatically selected based on pre-processing of the image data. For example, a default hanging protocol may be selected based on CAD findings of image data, as described above. However, a default hanging protocol may be selected based on any other pre-processing functions applied to image data. Pre-processing functions generally are image-processing functions that prepare an image for presentation to a user.

Once the default hanging workflow has been communicated to display workstation 140, display workstation 140 may apply the default hanging protocol to the images. For example, a default hanging protocol may direct display workstation 140 to display a PA image adjacent to a lateral image of a patient anatomy.

In another embodiment of the present invention, a default hanging protocol may direct display workstation 140 to display images corresponding to image data recently acquired in addition to images corresponding to image data previously acquired. For example, a hanging protocol may direct a workstation 140 to present the most recently acquired images first, followed by older images. The older images may be stored locally on a memory of workstation 140 and/or memory 220 of server 130.

In another embodiment of the present invention, a default hanging protocol may direct display workstation 140 to display laboratory results or data along with one or more images. For example, a default hanging protocol may direct display workstation 140 to display a series of images in sequential order, followed by a screen that displays text corresponding to laboratory results. The text may be displayed alone on a display device, adjacent to one or more images, or on one or more images, for example. In general, the laboratory results are germane to one or more CAD findings.

Figure 3:
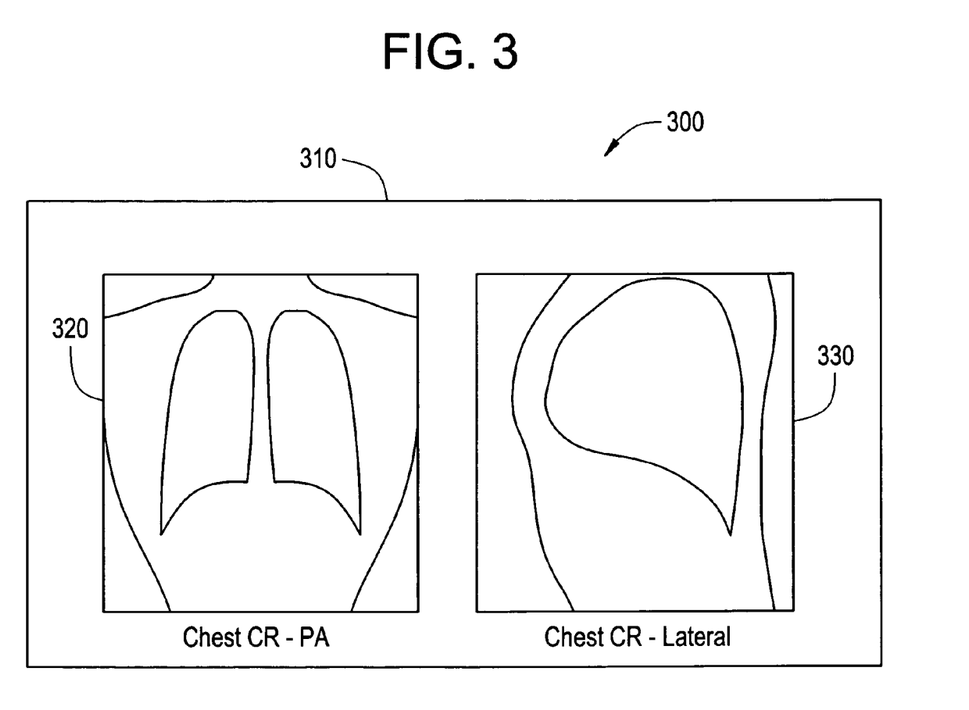
FIG. 3 illustrates a first display of images on a display screen of a workstation in accordance with an embodiment of the present invention.
Figure 4:
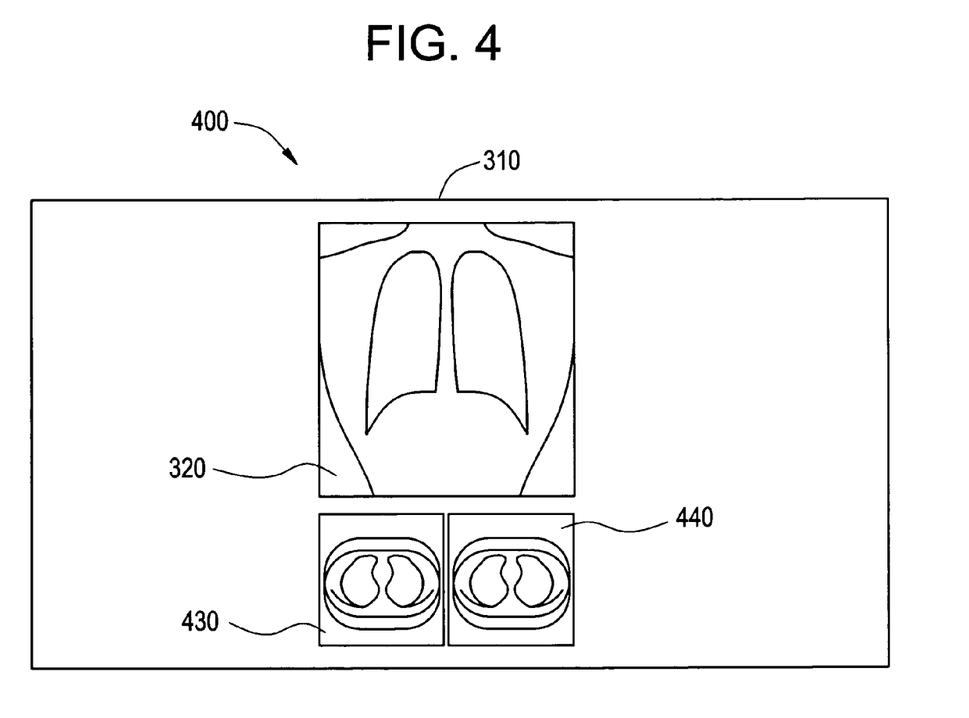
FIG. 4 illustrates a second display of images on the display screen in accordance with an embodiment of the present invention.
Figure 5:
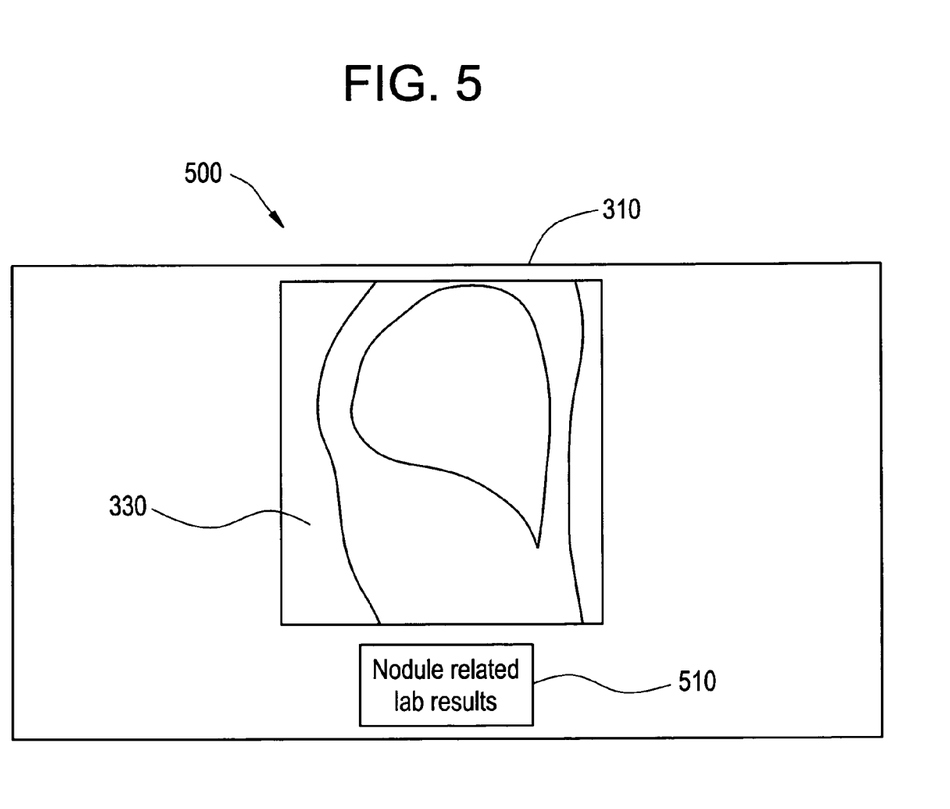
FIG. 5 illustrates a third display of an image and laboratory results on the display screen in accordance with an embodiment of the present invention.

The use of hanging protocols to display images is exemplified in FIGS. 3 through 5. FIG. 3 illustrates a first display 300 of images 320, 330 on a display screen 310 of a workstation 140 in accordance with an embodiment of the present invention. First display 300 illustrates the presentation of two images 320, 330 on a screen 310 of workstation 140. Screen 310 may be embodied in any display device capable of presenting images derived from electronic image data. For example, screen 310 may be a liquid-crystal display ("LCD") screen, a computer monitor, or a television monitor.

Images 320 and 330 were recently acquired of a patient's lungs using a C-arm x-ray imaging device. Image 320 is a PA image of the lungs and image 330 is a lateral image of the lungs. After the images were acquired, a default hanging protocol is selected and the display rules of the hanging protocol are applied to the images 320, 330. As described above, a hanging protocol includes display rules that direct display workstation 140 to present images 320, 330 in a particular temporal and/or spatial layout or sequence. Also as described above, the default hanging protocol may be selected from a plurality of default hanging protocols in any number of ways. In FIG. 3, the display rules of the hanging protocol have directed workstation 140 to present the PA image 320 adjacent and to the left of the lateral image 330.

Next, the display rules of the hanging protocol direct workstation 140 to present a second display 400. FIG. 4 illustrates a second display 400 of images 320, 430, 440 on display screen 310 in accordance with an embodiment of the present invention. As described above, image 320 is a PA image. Images 430 and 440 are multi-slice CT images of the patient's lungs. The display rules of the hanging protocol have directed workstation 140 to present the multi-slice CT images 430, 440 adjacent to each other and below the PA image 320.

Next, the display rules of the hanging protocol direct workstation 140 to present a third display 500. FIG. 5 illustrates a third display 500 of image 330 and laboratory results 510 on display screen 310 in accordance with an embodiment of the present invention. As described above, image 330 is a lateral image of the lungs. Laboratory results 510 can include any presentation (for example, text) of laboratory test results germane to any of the images presented on screen 310 and/or a diagnosis performed by a radiologist, for example. The display rules of the hanging protocol have directed workstation 140 to present the lateral image 330 adjacent to and above laboratory results 510.

FIGS. 3 through 5 thus present an example of how display rules in a hanging protocol may be invoked to present a plurality of images and laboratory data at a display workstation 140, in accordance with an embodiment of the present invention. The display rules may be highly customizable in order to present images and/or other data in any temporal and/or spatial layout or sequence that may assist a radiologist to perform an analysis and/or diagnosis on the images and/or data.

As described above, a user may wish to apply additional display rules to alter the temporal and/or spatial layout of images after a default hanging protocol is applied to the images. For example, a user may desire to present old and/or new images adjacent to each other, in a particular sequence, or in conjunction with the presentation of laboratory results. In another example, various users may have personal preferences for the layout and sequence of images that differs from a default hanging protocol. In other words, different users may wish to view images in various spatial and/or temporal layouts and sequences.

The additional display rule(s) may include any display rule useful to present an image for a diagnostic examination. A user may select additional display rules in any manner known to those of skill in the art. For example, a user may use an input device to manually select a display rule. The input device can include any one or more of a mouse, stylus, keyboard, and/or microphone, for example.

Once a user has selected an additional display rule, the display rule is applied to the image data. The additional display rule(s) may be stored on a memory 220 of server 130 and communicated to display workstation 140 when requested by a user.

In another embodiment of the present invention, the additional display rule(s) may be stored on a memory of display workstation 140 and applied at workstation 140 when requested by a user. In such an embodiment, a communication concerning the identity or type of display rule may be sent from workstation 140 to server 130.

Tracking routine 214 monitors the selection and/or application of one or more additional display rules. Tracking routine 214 may be embodied in a set of instructions stored on a computer-readable medium. For example, tracking routine 214 may be embodied in a software application stored at server 130.

In another embodiment of the present invention, tracking routine 214 can reside at workstation 140 and communicate the selection of one or more additional processing steps to server 130.

Tracking routine 214 can monitor the selection and/or application of one or more additional display rules by monitoring manual input from a user. For example, tracking device 214 can monitor a number of times a user selects a particular display rule and/or the number of times a particular display rule is applied at display workstation 140. In another example, tracking routine 214 may monitor a location on a display device of workstation 140 that an input device is used to select or invoke an additional display rule. In other words, if a user employs a mouse to move an on-screen pointer over a graphical representation of an additional display rule and then clicks the mouse to select the display rule, tracking routine 214 can monitor the location. Based on a look-up table or other manner of associating an on-screen location with a graphical representation of a display rule, tracking routine 214 can then determine which display rule was selected.

In another embodiment of the present invention, tracking routine 214 monitors a user's selection of a sequence of display rules. For example, in a given set of display rules A, B, C, D, E and F available for selection by a user, a user may repeatedly select 4 display rules in the same order, such as 1) B, 2) D, 3) A and 4) F. Tracking routine 214 may then monitor the number of times the user selects this sequence of display rules.

In another embodiment of the present invention, tracking routine 214 can monitor the selection and/or application of one or more additional display rules during a given time period. For example, tracking routine 214 may monitor the number of times a user selects a given display rule during a defined time period such as an 8 hour period or a time period defined by the user logging in and logging out of a workstation 140.

In another embodiment of the present invention, tracking routine 214 can monitor the selection and/or application of one or more additional display rules to a certain type or class of images. A type or class of images may be defined as one or more of: images obtained from the same or similar (for example, common) imaging modality, images used for a same or similar diagnostic exam, images featuring the same or similar type of anatomy, and images examined by a particular user identity, for example. For example, tracking routine 214 may monitor the number of times a user selects a given display rule for images obtained from the same imaging modality.

Tracking routine 214 may compare the number of times a user selects a particular display rule to a threshold in order to determine whether the default hanging protocol should be modified. If the user selects the particular display rule a number of times that is greater than a threshold, tracking routine 214 may notify modifying routine 216.

In another example, tracking routine 214 may compare the number of times a user selects a particular sequence of display rules (as described above) to a threshold. If the user selects the same or similar sequence of rules a number of times that is greater than a threshold, tracking routine 214 may direct modifying routine 216 to modify the default hanging protocol.

In another example, tracking routine 214 may compare the number of times a user employs an input device to activate a graphical representation of a display rule (at an on-screen location) to a threshold. If the user uses the input device to activate the display rule at the same or similar on-screen location a number of times that is greater than a threshold, tracking routine 214 may notify modifying routine 216. For example, tracking routine 214 may monitor or track where a user uses a mouse to move a graphical pointer on a computer screen.

In another embodiment of the present invention, tracking routine 214 may compare a user's selection(s) of display rule(s) to a plurality of thresholds in order to determine whether the default hanging protocol should be modified. For example, tracking routine 214 may monitor the number of times a single display rule is selected by a user in a given time period and a number of times a sequence of display rules is selected by a user. Tracking routine 214 may then compare the number of times the single display rule is selected by a user in a given time period to a first threshold and a number of times the sequence of display rules is selected by a user to a second threshold, for example. When either or both exceed the corresponding threshold, tracking routine 214 may notify modifying routine 216 of a need to modify the default hanging protocol.

In another embodiment of the present invention, one or more thresholds are global thresholds applicable to a group of users or to all users. That is, each user's selection of display rule(s) is compared to the same threshold in order to determine whether tracking routine 214 should notify modifying routine 216, for example.

In another embodiment of the present invention, one or more thresholds are individually customizable thresholds. That is, each user may set his or her thresholds to a number that he or she desires. In this way, each user has highly customizable control over when tracking routine 214 notifies modifying routine 216 of a need to modify the default hanging protocol.

In another embodiment of the present invention, one or more thresholds may be based on a user identity, an imaging modality from which the images are obtained, a type of diagnostic exam to be performed using the images, and an anatomy featured in the images. For example, thresholds may vary among different types of imaging modalities, users, diagnostic exams, and/or anatomies featured in images.

By monitoring a number of times a user selects the same or similar display rules (or a sequence of display rules) to be applied to a presentation of images at a display workstation 140 (in addition to the display rules of the default hanging protocol), tracking routine 214 is tracking rote, repetitive tasks that a user frequently selects. In other words, tracking routine 214 is monitoring when a user repeatedly applies the same or similar display rules to image data that has already been presented in a spatial and/or temporal layout or sequence according to the default hanging protocol. Tracking routine 214 thus monitors when a user is spending considerable amounts of time repeatedly selecting the same additional display rules. As such, the present invention modifies the default hanging protocol in order to incorporate the repeated display rules routinely selected by a given user.

The notification communicated from tracking routine 214 to modifying routine 216 (when a number of times a display rule and/or a number of times a sequence of display rules exceeds one or more thresholds) can include any communication sufficient to inform modifying routine 216 that the default hanging protocol needs to be modified. For example, tracking routine 214 may communicate an "EDIT" message to modifying routine 216 with instructions on which display rules need to be added to the default workflow or which display rules of the default workflow need to be altered.

Once modifying routine 216 receives a notification from tracking routine 214, modifying routine 216 modifies or edits the default hanging protocol. The modifying routine 216 may modify the default hanging protocol in any manner known to those of skill in the art. For example, modifying routine 216 may modify a default hanging protocol by altering one or more display rules, by adding at least one additional display rule to the default hanging protocol, and/or by adding a sequence of display rules to the default hanging protocol. For example, modifying routine 216 may edit the default hanging protocol by adding a particular display rule (frequently selected by a user) to the default hanging protocol. Similarly, modifying routine 216 may edit the default hanging protocol by adding a sequence of display rules that is frequently selected by a user to the default hanging protocol.

In another example, modifying routine 216 may edit the default hanging protocol by removing or altering a default display rule (included in the default hanging protocol) that is frequently undone or corrected for by a user. In other words, a default hanging protocol may direct workstation 140 to present recently acquired PA and lateral images adjacent to each other before presenting laboratory results adjacent to previously acquired PA and lateral images. If a user routinely follows the default hanging protocol by removing the presentation of laboratory results after the recently acquired images, then modifying routine 216 may edit the default hanging protocol to present the previously acquired images after the recently acquired images, with no presentation of laboratory data, for example.

In another embodiment of the present invention, modifying routine 216 obtains a user's permission before modifying a default hanging protocol. For example, modifying routine 216 may communicate a query to a user asking for permission to modify a default hanging protocol. The query can be communicated between server 130 and display workstation 140, for example. The query can include a recommended modification to the default hanging protocol and a request for permission to edit the default hanging protocol, for example. The user then may grant or deny editing permission to modifying routine 216. If the user grants editing permission, modifying routine 216 then edits the default hanging protocol. If the user denies editing permission, modifying routine 216 then does not edit the default hanging protocol.

In another embodiment of the present invention, modifying routine 216 may ensure that any modification to a default hanging protocol complies with a regulatory requirement. For example, the Food and Drug Administration ("FDA") may require that a particular sequence of images always be presented in a certain temporal and/or spatial layout or sequence. Modifying routine 216 can reference a list of regulatory requirements for some or all default hanging protocol stored at server 130 to ensure that a modification to a default hanging protocol does not cause a modified default hanging protocol to violate any regulatory requirements. If the modified default hanging protocol does not violate any regulatory requirements, modifying routine 216 then edits the default hanging protocol. If the modified default hanging protocol would violate one or more regulatory requirements, modifying routine 216 then does not edit the default hanging protocol and may include a communication to a user notifying him or her of this violation.

After a default hanging protocol is modified, modifying routine 216 communicates the modified default hanging protocol to memory 220. Thereafter, the modified default hanging protocol may be employed to present images at a display workstation 140 as a default hanging protocol. The new default hanging protocol may then be subsequently modified as explained above. Therefore, the present invention provides for the continuous dynamic improvement of a default hanging protocol such that a default hanging protocol is continually updated to accommodate repeated display rules selected by a user.

In another embodiment of the present invention, a modified default hanging protocol associated with a first user may be accessible to and used by at least one other user. For example, a first user may be an experienced radiologist. A second user may be a new, inexperienced radiologist. Any one or more of the modified default hanging protocols created by the experienced radiologist may be communicated from server 130 to a display workstation 140 for use by the inexperienced radiologist. As such, the inexperienced radiologist can learn from the modifications made to a default hanging protocol by the experienced radiologist.

Figure 6:
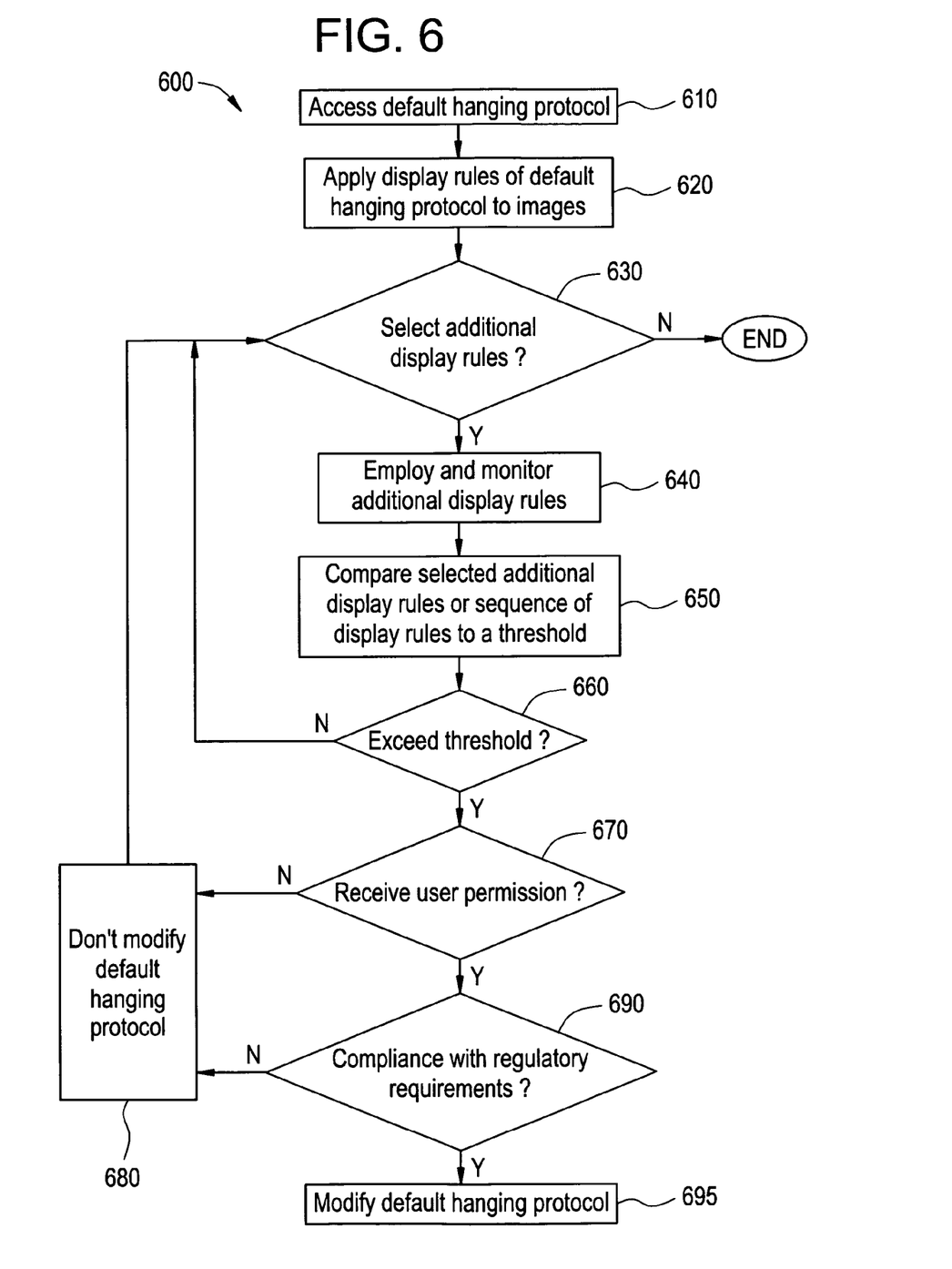
FIG. 6 illustrates a flowchart for a method for dynamically altering a hanging protocol in accordance with an embodiment of the present invention.

FIG. 6 illustrates a flowchart for a method 600 for dynamically altering a hanging protocol in accordance with an embodiment of the present invention. First, at step 610, a default hanging protocol is accessed, as described above. For example, a default hanging protocol may be communicated from memory 220 in server 130 to one or more display workstations 140.

Next, at step 620, the default display rules included in the default hanging protocol are employed to present a plurality of images at one or more workstations 140, as described above.

Next, at step 630, a determination is made whether additional display rules are selected to alter the presentation of the images at the workstation(s) 140. In other words, method 600 determines, at step 630, whether display rules in addition to those of the default hanging protocol are selected to alter a temporal and/or spatial layout or sequence of the images at the workstation 140. If no additional display rules are selected, the images are presented to a user at display workstation 140 in accordance with the display rules of the default hanging protocol and method 600 terminates.

If additional display rules are selected, method 600 proceeds to step 640. At step 640, the additional display rules are employed to alter the presentation of images at workstation 140. In other words, the additional display rules are used to change a spatial and/or temporal layout or presentation of the images. In addition, the additional display rules are monitored. As described above, a tracking routine or device 214 can track which display rules are selected, for example. Also as described above, in another embodiment of the present invention, at step 640, additional display rules selected by a user for a class of image data (defined by, for example, the imaging modality used to obtain the images, the type of diagnostic examination to be performed on the images, the anatomy featured in the images, and/or the identity of the user accessing the images) may be monitored. A selection of additional display steps may therefore be monitored not just for a singular set of images, but also for all images obtained by a particular imaging modality or accessed by a given user, for example.

Next, at step 650, the number of times a particular display rule is selected and/or a sequence of additional display rules is selected are compared to one or more thresholds, as described above.

Next, at step 660, method 600 determines whether the number of times a particular display rule is selected or the number of times a sequence of display rules is selected exceeds one or more thresholds. For example, if a given sequence of display rules is selected by a user 21 times and is compared to a threshold of 20 times, then step 660 determines that at least one threshold has been exceeded. If the number of times a given display rule is selected or the number of times a sequence of display rules is selected does not exceed one or more thresholds, then method 600 proceeds to step 630.

However, if it is determined that the number of times a given display rule is selected or the number of times a sequence of display rules is selected exceeds one or more thresholds at step 660, then method 600 proceeds to step 670.

At step 670, a user is prompted for permission to modify the default hanging protocol, as described above. If the user denies permission, method 600 proceeds to step 680, where the default hanging protocol is not modified. Method 600 then proceeds to step 630.

However, if the user grants permission at step 670, then method 600 proceeds to step 690. At step 690, method 600 determines if the proposed modification to the default hanging protocol causes the default hanging protocol to violate or fail to comply with one or more regulatory requirements, as described above. If the proposed modification would cause such a violation, method 600 proceeds to step 680, where the default hanging protocol is not modified. Method 600 then proceeds to step 630.

However, if the proposed modification would not cause the default hanging protocol to violate a regulatory requirement, method 600 proceeds to step 695. At step 695, the default hanging protocol is modified in accordance with the proposed modification, as described above.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features that come within the spirit and scope of the invention.

What is claimed is:

1. A computer-readable storage medium including a set of instructions for a computer, said instructions including:
   an access routine communicating a default hanging protocol between a network server and a display workstation, said default hanging protocol including at least one default display rule for displaying a plurality of images at said display workstation, said default display rule directing said display workstation to present each of said images at a location on a display device of said display workstation and/or in a sequence in which each of said images is presented at said display workstation;
   a tracking routine monitoring a selection of an additional display rule, wherein said tracking routine monitors repeated manual selection of said additional display rule over time by a user; and
   a modifying routine dynamically modifying said default hanging protocol based on said selection, wherein said modifying routine incorporates said repeated manual selection of said additional display rule over time by the user into said default hanging protocol such that said default hanging protocol is modified to comprise said additional display rule, wherein said modifying routine eliminates a need for said repeated manual selection of said additional display rule.

2. The computer-readable storage medium of claim 1, wherein said modifying routine is configured to dynamically modify said default hanging protocol by altering said default display rule of said default hanging protocol and/or adding said additional display rule to said default hanging protocol.

3. The computer-readable storage medium of claim 1, wherein said additional display rule is selected in order to alter one or more of:
   said location at which each of said images is presented on said display device;
   a location at which an additional image is presented on said display device;
   said sequence in which each of said images is presented at said display workstation; and
   a sequence in which a plurality of additional images is presented at said display workstation.

4. The computer-readable storage medium of claim 1, wherein at least one of said default display rule and said additional display rule direct said display workstation to present said images for a diagnostic examination of a patient anatomy featured in said images.

5. The computer-readable storage medium of claim 1, wherein said access routine is configured to select said default hanging protocol from a plurality of default hanging protocols and communicate said default hanging protocol based on one or more of:
   a pre-processing function applied to said images prior to display at said display workstation; and
   a result of a computer-aided diagnosis based on at least one of said images.

6. The computer-readable storage medium of claim 1, wherein said access routine is configured to communicate said default hanging protocol through a network connection.

7. The computer-readable storage medium of claim 1, wherein said tracking routine is configured to monitor one or more of a number of times said additional display rule is selected and a number of times a sequence of a plurality of said additional display rules is selected.

8. The computer-readable storage medium of claim 7, wherein said modifying routine is configured to modify said default hanging protocol after one or more of:
   said number of times said additional display rule is selected exceeds one or more thresholds; and
   said number of times said sequence of said additional display rules is selected exceeds one or more of said thresholds.

9. The computer-readable storage medium of claim 8, wherein said one or more of said thresholds are individually customizable.

10. The computer-readable storage medium of claim 1, wherein said modifying routine is configured to modify said default hanging protocol after a user is prompted for and provides permission to modify said default hanging protocol.

11. The computer-readable storage medium of claim 1, wherein said modifying routine is configured to make a modification to said default hanging protocol in order to create a modified default hanging protocol, wherein said modification is based on at least a manual selection of said additional display rule by a user and said access routine is configured to communicate said modified default hanging protocol to at least one other user.

12. A method for dynamically altering a default hanging protocol, said method including:

providing access to said default hanging protocol, said default hanging protocol including at least one display rule, said display rule employed to direct a display workstation to present each of a plurality of images in a location on a display device and/or in a sequence in which each of said images is presented on said display device;

providing a tracking system monitoring a selection of at least one additional display rule;

monitoring, by the tracking system, repeated manual selection of said at least one additional display rule over time;

providing a hanging protocol editor capable of dynamically creating a modified default hanging protocol, said modified default hanging protocol including said default hanging protocol and a modification to said default hanging protocol, said modification based on at least said repeated manual selection of said at least one additional display rule; and incorporating, through the hanging protocol editor, said repeated manual selection of said at least one additional display rule over time into said default hanging protocol such that said modified default hanging protocol comprises said at least one additional display rule, wherein said incorporating eliminates a need for said repeated manual selection.

13. The method of claim 12, wherein said step of providing access includes providing a set of instructions stored on a computer-readable storage medium capable of being communicated between a server and a display workstation, said set of instructions capable of performing said steps of providing said tracking system and providing said hanging protocol editor.

14. The method of claim 12, wherein said at least one additional display rule is selected in order to alter one or more of:

said location at which each of said images is presented on said display device;

a location at which an additional image is presented on said display device;

said sequence in which each of said images is presented at said display workstation; and a sequence in which a plurality of additional images is presented at said display workstation.

15. The method of claim 12, wherein said default hanging protocol is selected from a plurality of default hanging protocols based on one or more of:

a pre-processing function applied to at least one of said images; and a computer-aided diagnosis of at least one of said images.

16. The method of claim 12, wherein said step of providing access includes providing access to said default hanging protocol after an identity of a user is authorized.

17. The method of claim 12, wherein said step of providing said tracking system includes said tracking system being capable of monitoring one or more of:

a number of times said at least one additional display rule is selected; and a number of times a sequence of a plurality of additional display rules is selected.

18. The method of claim 17, wherein said hanging protocol editor is capable of creating said modified default hanging protocol when one or more of:

said number of times said at least one additional display rule is selected exceeds one or more thresholds; and said number of times said sequence is selected exceeds one or more of said thresholds.

19. The method of claim 17, wherein said hanging protocol editor is capable of creating said modified default hanging protocol by one or more of:

adding said at least one additional display rule to said default hanging protocol;

removing at least one of said display rules from said default hanging protocol; and adding said sequence of said additional display rules to said default hanging protocol.

20. The method of claim 12, wherein said hanging protocol editor is capable of creating said modified hanging protocol after at least one of receiving permission from a user and ensuring that said modified default hanging protocol complies with a regulatory requirement.

21. A system for dynamically altering a hanging protocol in a picture archiving and communication system, said system including:

a default hanging protocol including a subset of a plurality of display rules, said display rules employed in determining a presentation of a plurality of images as displayed on a display device;

a tracking system configured to monitor a user's selection of one or more of said plurality of display rules outside of said subset to alter said presentation, wherein said tracking system monitors repeated manual selection of said one or more of said plurality of display rules outside of said subset over time; and a hanging protocol editor configured to modify said default hanging protocol based on at least said user's selection, wherein said hanging protocol incorporates said repeated manual selection of said one or more of said plurality of display rules outside of said subset over time into said default hanging protocol such that said modified default hanging protocol comprises said one or more of said plurality of display rules outside of said subset, wherein said modified default hanging protocol eliminates a need for said repeated manual selection of said one or more of said plurality of display rules outside of said subset.

22. The system of claim 21, wherein said display rules direct said display device to display each of said images according to said presentation, said presentation including one or more of a temporal and spatial layout of each of said images.

23. The system of claim 21, wherein said tracking system is configured to monitor one or more of a number of times said user selects a particular display rule and a number of times said user selects a sequence of display rules.

24. The system of claim 23, wherein said hanging protocol editor is configured to recommend at least one modification to said default hanging protocol based on one or more of said number of times said user selects said particular display rule and said number of times said user selects said sequence of display rules.

25. The system of claim 24, wherein said hanging protocol editor is configured to modify said default hanging protocol based on said modification after one or more of receiving permission from said user and ensuring that said modification does not violate a regulatory requirement.

26. The system of claim 21, wherein said tracking system is configured to monitor said selections of said display rules according to one or more of:

an imaging modality used to obtain each of said images;
a diagnostic exam performed using one or more of said images; and
an anatomy featured in each of said images.

* * * * *